(12) United States Patent
Bui

(10) Patent No.: US 8,012,510 B2
(45) Date of Patent: Sep. 6, 2011

(54) NUTRACEUTICAL FOR THE PREVENTION AND TREATMENT OF CANCERS AND DISEASES AFFECTING THE LIVER

(75) Inventor: Can V. Bui, Harvey, LA (US); Cuong Q. Bui, legal representative, Harvey, LA (US)

(73) Assignee: Canthao Corporation, Dewitt, NY (US)

( * ) Notice: Subject to any disclaimer, the term of this patent is extended or adjusted under 35 U.S.C. 154(b) by 554 days.

(21) Appl. No.: 10/560,558

(22) PCT Filed: Jun. 10, 2004

(86) PCT No.: PCT/US2004/018380
§ 371 (c)(1),
(2), (4) Date: May 8, 2008

(87) PCT Pub. No.: WO2004/112483
PCT Pub. Date: Dec. 29, 2004

(65) Prior Publication Data
US 2008/0213386 A1 Sep. 4, 2008

(51) Int. Cl.
*A61K 36/23* (2006.01)
(52) U.S. Cl. ......... 424/537; 424/744; 424/755; 424/725
(58) Field of Classification Search .................. None
See application file for complete search history.

(56) References Cited

U.S. PATENT DOCUMENTS
6,299,925 B1  10/2001  Xiong et al.

FOREIGN PATENT DOCUMENTS

| CN | 1127124 | * | 7/1996 |
|---|---|---|---|
| JP | 59227279 A | | 12/1984 |
| JP | 2000-083654 | * | 3/2000 |
| JP | 2001-299305 | * | 10/2001 |
| WO | WO 01/97823 | * | 12/2001 |
| WO | WO-2004-112483 A1 | | 12/2004 |

OTHER PUBLICATIONS

Katikova (Eksperimental'naia i klinicheskaia farmakologiia, (Jan.-Feb. 2002) vol. 65, No. 1, pp. 41-43).*
Lomnitski (Toxicologic Pathology (2000), vol. 28, No. 4, pp. 380-387).*
Aguayo, Alvaro and Patt, Yehuda Z., "Liver Cancer," Clinics in Liver Disease vol. 5(2):479-507 (2001).
Aguayo, Alvaro and Patt, Yehuda Z., "Liver Tumors: Nonsurgical Treatment of Hepatocellular Carcinoma," Clinics in Liver Disease vol. 5 (1):175-189 (2001).
Arase, Yasuji et al., "The Long Term Efficacy of Glycyrrhizin in Chronic Hepatitis C Patients," Cancer vol. 79 (8): 1494-1500 (1997).
Barnett, Jr., Carlton C. and Curley, Steven A., "Ablative Techniques for Hepatocellular Carcinoma," Seminars in Oncology vol. 28(5):487-496 (2001).
Carr, Brian I. et al., K Vitamins, PTP Antagonism, and Cell Growth Arrest, J. Cell. Physiol. 193:263-274 (2002).
Corsi, M.M. et al., "The Therapeutic Potential of Aloe Vera in Tumor-Bearing Rats," Tissue Reactions XX(4):115-118 (1998).
Dragnev, Konstantin H. et al., "The Retinoids and Cancer Prevention Mechanisms," The Oncologist 5:361-368 (2000).
Fenech, M., "Micronutrients and genomic stability: a new paradigm for recommended dietary allowances (RDAs)," Food and Chemical Toxicology 40:1113-1117 (2002).
Fenech, Michael, "Recommended dietary allowances (RDAs) for genomic stability," Mutation Research 480-481:51-54 (2001).
Georgiades, Christos S. et al., "New Nonsurgical Therapies in the Treatment of Hepatocellular Carcinoma," Techniques in Vascular and Interventional Radiology 4(3):193-199 (2001).
Giovannini, M. et al., "Hepatocellular carcinoma," Br. J. Cancer 84(Suppl.2):74-77 (2001).
He, Youping et al., Effects of Carotenoid-Rich Food Extracts on the Development of Preneoplastic Lesions in Rat Liver and on In Vivo and In Vitro Antioxidant Status, Nutrition and Cancer 27(3):238-244 (1997).
Kang, Jiu-Hong et al., "Effects of ascorbic acid and DL-α-tocopherol on humanhepatoma cell proliferation and redifferentiation," Acta Pharmacol. Sin. 21(4):348-352 (2000).
Kang, Jiu-Hong et al., "Effects of ascorbic acid on human hepatoma cell proliferation and redifferentiation," Acta Pharmacol. Sin. 20(11):1019-1024 (1999).
Kashef, Elika and Roberts, John P., "Transplantation for Hepatocellular Carcinoma," Seminars in Oncology 28(5):497-502 (2001).
Kew, M.C., "Hepatitis viruses and hepatocellular carcinoma," Res. Virol. 149:257-262 (1998).
Kuo, Po-Lin et al., "The antipoliferative activity of aloe-emodin is through p53-dependent and p21-dependent apoptotic pathway in human hepatoma cell lines," Life Sciences 71:1879-1892 (2002).
Kuyvenhoven, J. Ph. et al., "Practical Management of Hepatocellular Carcinoma," Scand. J. Gastroenterol. Suppl 234:82-87 (2001).
Lee, Simon Ming Yuen et al., "Paeoniae Radix, a Chinese herbal extract, inhibit hepatoma cells growth by inducing apoptosis in a p53 independent pathway," Life Sciences 72:2267-2277 (2002).
Lee, KwangYoul et al., "Aloesin up-regulates cyclin E/CDK2 kinase activity via inducing the protein levels of cyclin E, CDK2, and CDC25A in SK-HEP-1 cells," Biochem. and Mol. Biol. International 41(2):285-292 (1997).
Leung, Thomas W.T. and Johnson, Philip J., "Systemic Therapy for Hepatocellular Carcinoma," Seminars in Oncology 28(5):514-520 (2001).

(Continued)

*Primary Examiner* — Susan C Hoffman
(74) *Attorney, Agent, or Firm* — Wilson Sonsini Goodrich & Rosati

(57) ABSTRACT

A composition comprising vegetable/herbal-based dietary ingredients, or extracts, which contains vitamins and nutrients that provide a novel nontoxic treatment for liver cancers, hepatitis, and liver cirrhosis. The composition can be taken as a daily dietary supplement to enhance normal physiological functions of the body. The said composition, or extracts thereof, are useful and effective in the treatment and prevention of liver and possibly other cancers. The compositions are also useful for administration to patients with pre-existing hepatitis and/or liver cirrhosis. The compositions or extracts thereof may be useful for treating other cancers and other disorders, diseases, or conditions.

13 Claims, 6 Drawing Sheets

OTHER PUBLICATIONS

Little, Sarah A. and Fong, Yuman, "Hepatocellular Carcinoma: Current Surgical Management," Seminars in Oncology 28(5):474-486 (2001).

Meyskens, Frank L. et al., "Phase II trial of oral β-all trans-retinoic acid in hepatocellular carcinoma (SWOG 9157)," Investigational New Drugs 16:171-173 (1998).

Moradpour, Darius et al, "Hepatitis C: an update," Swiss Med. Wkly. 131:291-298 (2001).

Moradpour, D. et al., Hepatitis C: A concise review, Minerva Med. 92:329-339 (2001).

Moriwaki, Hisataka et al., "Nutritional pharmacotherapy of chronic liver disease: from support of liver failure to prevention of liver cancer," J. Gastroenterol. 35(Suppl XII):13-17 (2000).

Muto, Yasutoshi et al., "Prevention of second primary tumors by an acyclic retinoid, polyprenoic acid, in patients with hepatocellular carcinoma," New England J. of Med. 334(24):1561-1567 (1996).

Naccarato, R. and Farinati, F., "Hepatocellular Carcinoma, Alcohol, and Cirrhosis: Facts and Hypotheses," Digestive Diseases and Sciences 36(8):1137-1142 (1991).

Nakamura, Noriaki et al., "Apoptosis inHuman Hepatoma Cell Line Induced by 4,5-Didehydrogeranylgeranoic Acid (Acyclic Retinoid) via Down-Regulation of Transforming Growth Factor-α," Biochem. and Biophys. Res. Comm. 219:100-104 (1996).

Ni, Runshou et al., "Cell Growth Inhibition by a Novel Vitamin K Is Associated with Induction of Protein Tyrosine Phosphorylation," J. of Biol. Chem. 273(16):9906-9911 (1998).

Nishikawa, Yuji et al., "Inhibition of Hepatoma Cell Growth in Vitro by Arylating and Non-arylating K Vitamin Analogs," J. of Biol. Chem. 274(49):34803-34810 (1999).

Nishikawa, Yuji et al., "Growth Inhibition of Hepatoma Cells Induced by Vitamin K and Its Analogs," J. of Biol. Chem. 270(47):28304-28310 (1995).

Okuno, Masataka et al., "Chemoprevention of hepatocellular carcinoma: Concept, progress and perspectives," J. Gastroenterol. And Hepatol. 16:1329-1335 (2001).

Puatanachokchai, Rawiwan et al., "Inhibitory effects of lemon grass (Cymbopogon citratus, Stapf) extract on the early phase of hepatocarcinogenesis after initiation with diethylnitrosamine in male Fischer 344 rats," Cancer Letters 183:9-15 (2002).

Rieder, A. et al., "Delay of Diethylnitrosamine-Induced Hepatoma in Rats by Carrot Feeding," Oncology 40:120-123 (1983).

Ross, Ronald K. et al., "Urinary aflatoxin biomarkers and risk of hepatocellular carcinoma," The Lancet 339 (8799):943-946 (1992).

Sakagami, Hiroshi et al., Apoptosis-Inducing Activity of Vitamin C and Vitamin K, Cellular and Molecular Biol. 46(1):129-143 (2000).

Sakaida, Isao et al., "Herbal medicine Sho-saiko-to (TJ-9) prevents liver fibrosis and enzyme-altered lesions in rat liver cirrhosis induced by a choline-deficient L-amino acid-defined diet," J of Hepatology 28:298-306 (1998).

Seitz, Helmut et al., "Alcohol and Cancer," Recent Developments in Alcoholism 14: The Consequences of Alcoholism, edited by Galanter,Plenum Press U.S.A., pp. 67-95 (1998).

Shamaan, Nor Aripin et al., "Vitamin C and Aloe Vera Supplementation Protects from Chemical Hepatocarcinogenesis in the Rat," Nutrition 14 (Nov. 12): 846-852 (1998).

Shimizu, Satoshi et al., "Liver and Biliary, High prevalence of antibody to hepatitis C virus in heavy drinkers with chronic liver diseases in Japan," J. Gastroenterol. And Hepatology 7:30-35 (1992).

Stolz, Donna Beer and Michalopoulos, Michael, "Differential Modulation of Hepatocyte Growth Factor-Stimulated Motility by Transforming Growth Factor β1 on Rat Liver Epithelial Cells In Vitro," J Cell. Physiol. 175:30-40 (1998).

Suzui, Masumi et al., "Growth Inhibition of Human Hepatoma Cells by Acyclic Retinoid Is Associated with Induction of $p21^{CIP1}$ and Inhibition of Expression of Cyclin Dl[1]," Cancer Res. 62:3997-4006 (2002).

Thatte, Urmila et al., "Modulation of programmed cell death by medicinal plants," Cellular and Molecular Biol. 46(1):199-214 (2000).

Treiber, G., "Systemic Treatment of Hepatocellular Carcinoma," Dig. Dis. 19:311-323 (2001).

Wang, D.L. et al., "Analysis of 70 Cases of Primary Liver Carcinoma Treated by Pu Tuo Plaster and Herbs" Zhong Xi Yi Jie He Za Zhi 10(12):723-725 (1990) Abstract.

Wu, Lii-Tzu and Chung, Jing-Gung, "Effects of Vitamin C on Arylamine N-Acetyltransferase Activity in Human Liver Tumor Cells," Anticancer Res. 18:3481-3486 (1998).

Zhang, Yuesheng et al., "A major inducer of anticarcinogenic protective enzymes from broccoli: Isolation and elucidation of structure," PNAS USA 89:2399-2403 (1992).

Zheng, Q.S. and Zheng, R.L., "Effects of ascorbic acid and sodium selenite on growth and redifferentiation in human hepatoma cells and its mechanisms," Pharmazie 57(4): 265-269 (2002).

Encyclopedia of Foods: A Guide to Healthy Nutrition, Academic Press, copyright 2002 by Dole Food Company, Inc., 8 pages.

PCT/US04/18380 Search Report mailed Nov. 8, 2004.

* cited by examiner

Fig. #1
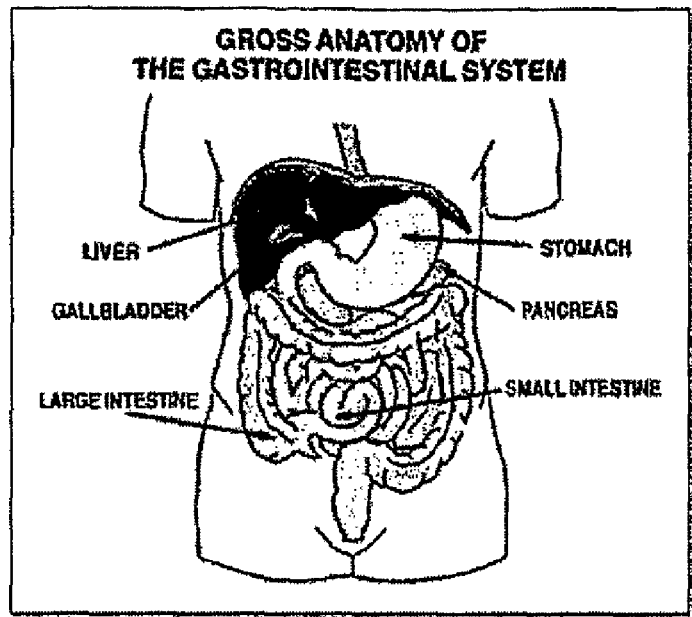
Fig. #2
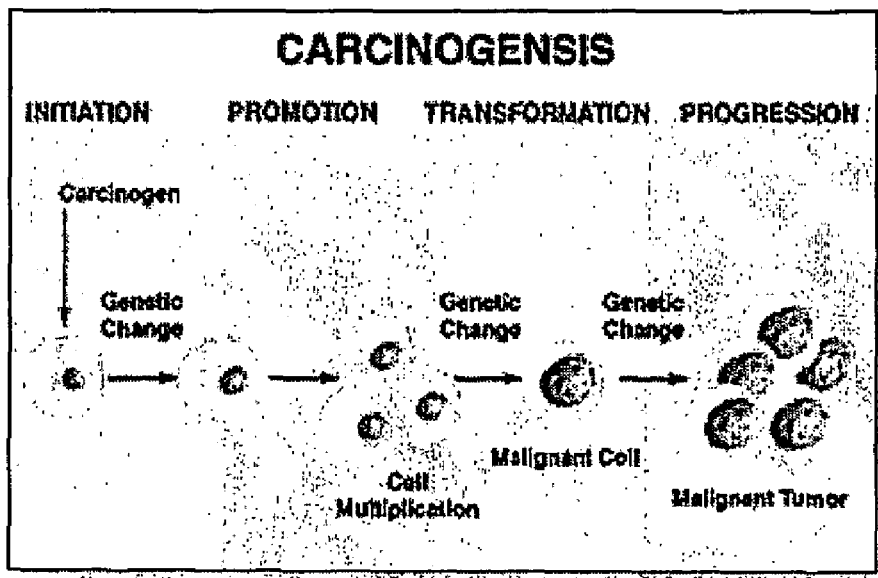

Fig. #3
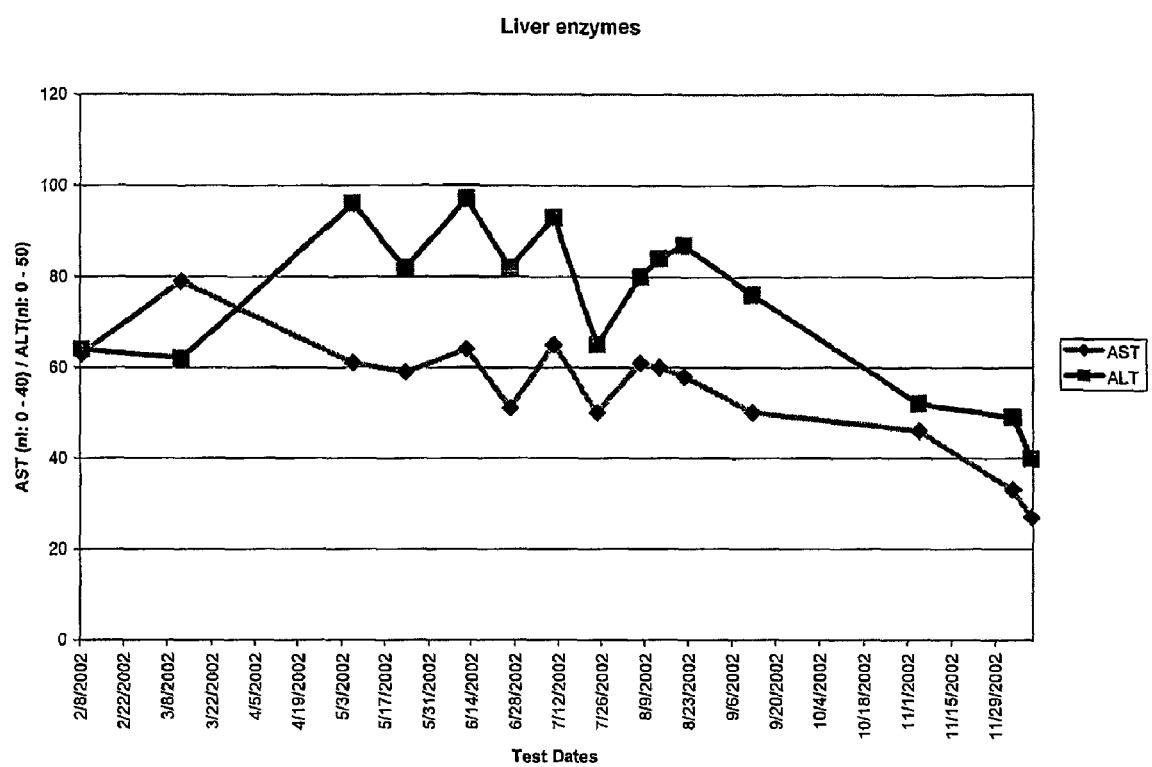

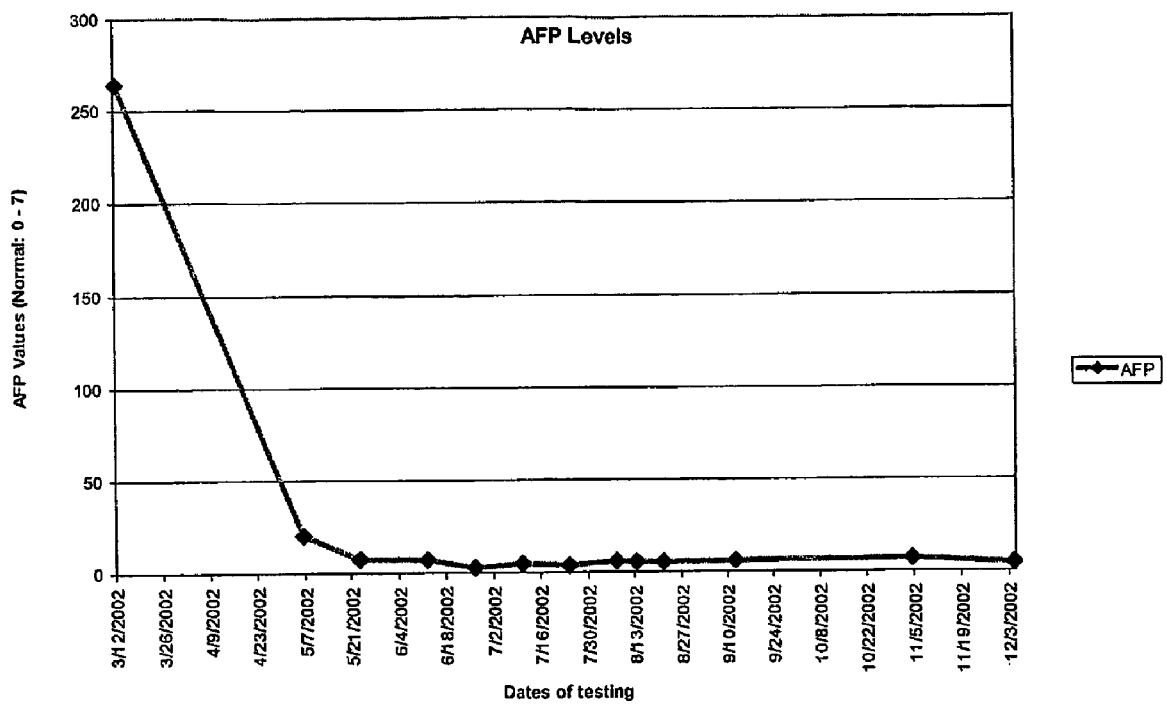
Fig. #4

Fig. #5
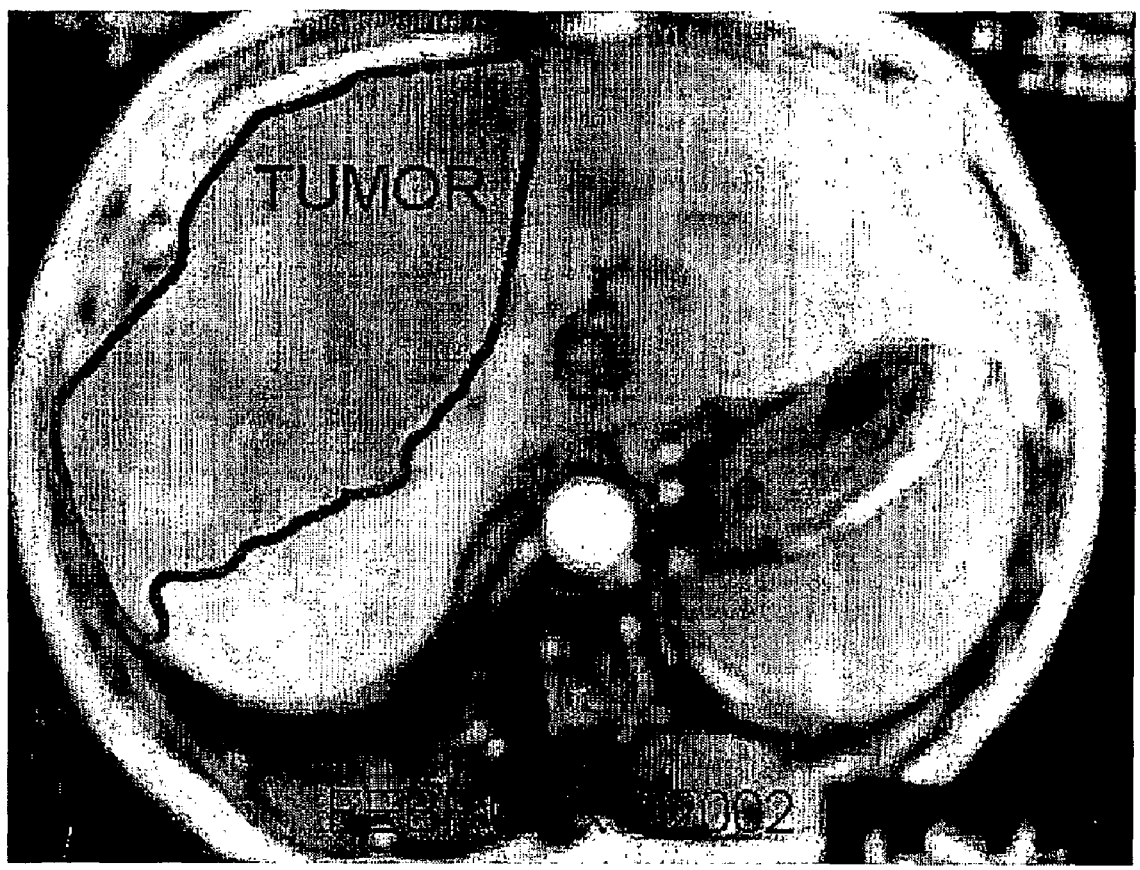

Fig. #6
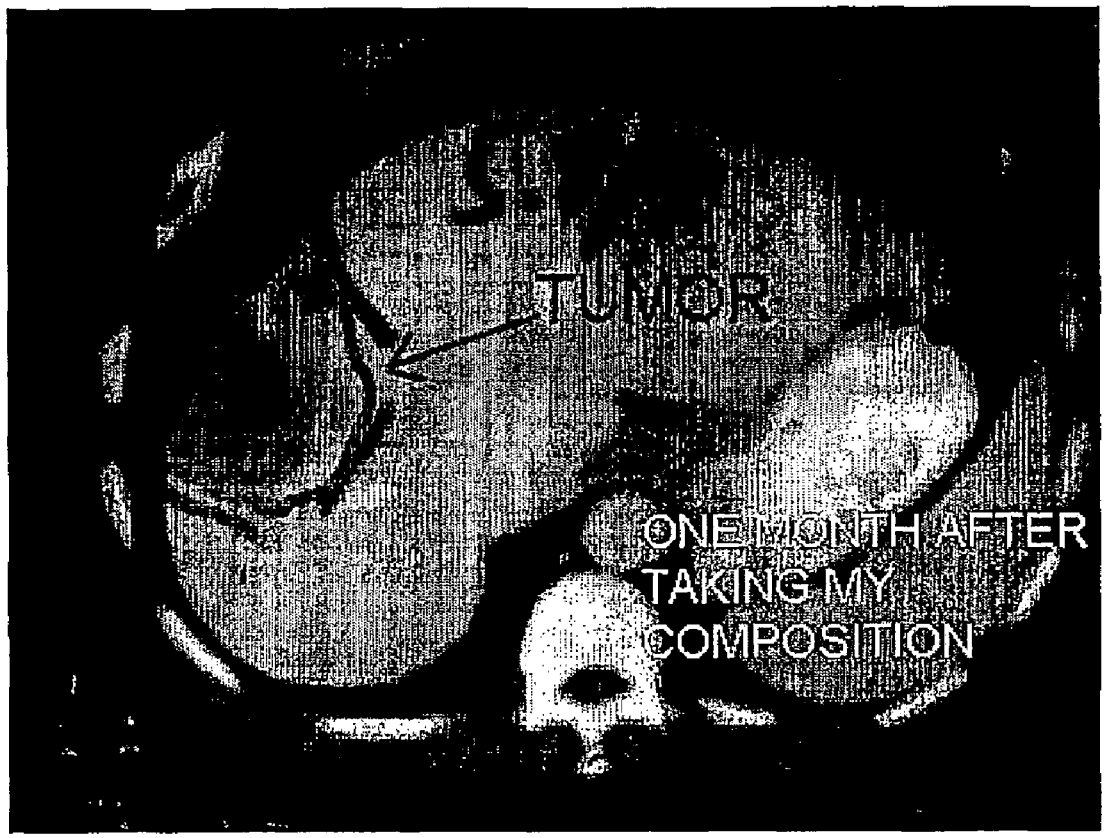

Fig. #7
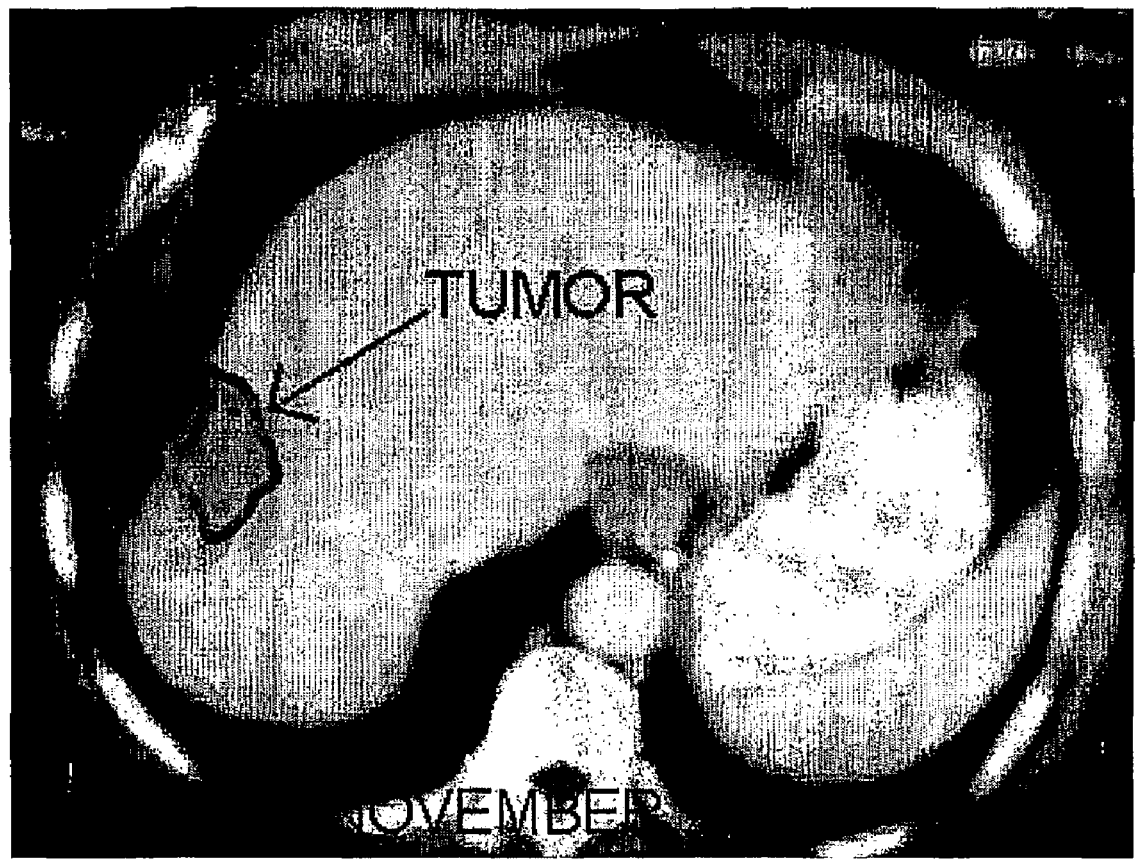

NUTRACEUTICAL FOR THE PREVENTION AND TREATMENT OF CANCERS AND DISEASES AFFECTING THE LIVER

FIELD OF TEE INVENTION

The present invention relates to organically-derived compositions and methods for administration of the compositions that are effective in the prevention and treatment of primary liver cancer and other diseases of the liver. The compositions are effective, for example, for the treatment of liver cirrhosis and/or chronic hepatitis of viral or non-viral etiology, and other diseases that may predispose a patient to the development of liver cancer. The compositions may also be effective in the treatment of other hepatobiliary disorders. In addition, the compositions may be effective in treatment of other liver diseases. The compositions may also be effective for the treatment of gastrointestinal cancer and other diseases. The compositions may also be used as a nutritional supplement to promote general health.

THE BACKGROUND OF THE INVENTION

The liver is the second largest organ in the body. Anatomically, the liver is located in the abdominal cavity below the right diaphragm with the gallbladder and duodenum below and the stomach flanked to the left. See FIG. 1 for an illustration of its anatomical relationship to other organs in the abdomen. The liver's blood supply system is unique. It has a dual blood supply system—blood is supplied via both the hepatic artery and the portal vein. The liver is the first organ to receive a nutrient-enriched blood supply from the digestive tract's portal circulation. Its unique vascular architecture provides unparalleled access to nutrients and xenobiotics absorbed through the digestive tract.

The liver plays critical roles in a myriad of metabolic pathways and synthetic functions of the body. Processing and redistribution of metabolic fuels such as glucose and fatty acids are major responsibilities of the liver. Diverse biochemical pathways in the liver modify and detoxify compounds absorbed from the intestine. The liver is the major synthetic site for serum proteins involved in coagulation, transport proteins such as albumin, iron binding proteins, and protease inhibitors. The liver is also the major site for synthesis of acute-phase reactants, a diverse group of proteins that are expressed during acute and chronic systemic inflammation. The functions of these proteins include roles in host defense against tissue damage and infection.

The liver also possesses the unique capacity to undergo rapid regeneration and replacement of damaged or dead cells within itself (Stolz, D. B. and G. K. Michalopoulos (1998), "Differential modulation of hepatocyte growth factor-stimulated motility by transforming growth factor beta1 on rat liver epithelial cells in vitro." *J Cell Physiol* 175(1): 30-40).

Diseases of the liver affect millions of people worldwide and kill tens of thousands on a daily basis. The largest groups of liver disease are liver cancer, cirrhosis, and hepatitis of the liver. The pathophysiology of these diseases are well studied, but treatment options remain poor and there are currently no definitive cures.

Cancers of the Liver

Cancers of the liver can be divided into two major categories; primary and metastatic. Primary liver cancers arise from within the liver itself, from hepatocytes (hepatocellular carcinoma), bile duct epithelium (hepatobiliary carcinoma), or mesenchymal tissue (angiosarcoma). Metastatic liver cancers arise from distant sources and secondarily spread to the liver through either the blood stream (hematogenous metastasis) or rarely through direct extension from a neighboring organ. Of the primary liver cancers, the most common is hepatocellular carcinoma (Kew, M. C. (1998). "Hepatitis viruses and hepatocellular carcinoma." *Res Virol* 149(5): 257-62).

Hepatocellular cancer arises from the epithelial cells of the liver called hepatocytes. Malignant changes in heptocytes cause uncontrolled proliferation of monoclonal or polyclonal cells that result in nodular, massive or diffuse pathologic varieties of hepatocellular cancer. Eventually, proliferation of the tumor results in functional compromise of the liver and metastatic spread to lungs and other organs. Death is usually from a combination of liver failure and disseminated cancer-induced multi-organ failure (Aguayo, A. and Y. Z. Patt (2001). "Liver cancer." *Clin Liver Dis* 5(2): 479-507).

Hepatocellular carcinoma is the seventh most common cancer in men and ninth in women, causing between 310,000 to 1 million new cases each year (Aguayo and Patt 2001). Hepatocellular cancer is the world's most common, solid-organ malignancy and is responsible for over 1 million deaths annually (Aguayo and Patt 2001). Men are generally more susceptible than women to hepatocellular carcinoma. Male predominance is more obvious in populations at high risk (mean ratio 3.7:1) (Kew 1998). The incidence of hepatocellular carcinoma generally rises progressively with age, although it tends to level off in the oldest age groups. Diagnosis usually occurs between 50-70 years (Kew 1998). There is a geographic predilection of hepatocellular cancer in East Asia and Sub-Saharan Africa (Kew 1998). In high-risk areas such as Southeast Asia, China, Japan, and sub-Saharan Africa the prevalence is greater than 100 per 100,000 population. In the U.S., there are 20,000 new cases of liver cancer diagnosed per year and over 15,000 attributed deaths per year (Aguayo and Patt 2001).

Hepatocarcinogenesis is a complex incremental process that usually evolves over many years (see FIG. 2). Four major (and several minor) causal associations of the tumor have been identified. These vary in importance based on prevalence of risk factors in different geographic locations. The four major factors include 1) chronic hepatitis-B infection, 2) chronic hepatitis-C infection, 3) exposure to aflatoxin and 4) cirrhosis of the liver. Minor factors that have been linked to the incidence of liver cancer include oral contraceptives, cigarette smoking, and a variety of inherited metabolic disorders and membranous obstruction of inferior vena cava (Kew 1998).

Hepatitis of the Liver

Hepatitis is an inflammation of the liver that causes liver damage and dysfunction. Hepatitis can result from a viral infection or from a variety of non-viral etiologies. However, the most common cause of hepatitis is from viral infections. Of the many viruses that cause hepatitis, Hepatitis B and C viruses are the two most common causes of hepatitis and the most strongly associated with development of hepatocellular cancer (Moradpour, D., A. Cerny, et al. (2001). "Hepatitis C: an update." *Swiss Med Wkly* 131(21-22): 291-8; Moradpour, D., B. Wolk, et al. (2001). "Hepatitis C: a concise review." *Minerva Med* 92(5): 329-39). Although infection with either of these viruses can cause severe, acute liver damage and resultant fulminant hepatic failure and death, most cases result in chronic inflammation. Chronic inflammation is manifested by moderate elevations in the hepatic enzymes Aspartate aminotransferase (AST) and Alanine aminotransferase (ALT), which are markers of ongoing hepatocellular injury and hepatocyte death. Approximately 80% of hepatocellular cancers are associated with chronic hepatitis-B infection (Kew 1998). Furthermore, as many as 50% of patients with chronic hepatitis-B infection will go on to develop cirrhosis and hepatocellular cancer. Chronic hepatitis-C infection is similarly implicated in development of hepatocellular cancer with some studies showing 83% of patients with this cancer have chronic infection. It is unclear if the two viruses act synergistically to promote carcinogenesis (Moradpour, Cerny et al. 2001; Moradpour, Wolk et al. 2001). In the U.S. there are 4 million people with chronic viral hepatitis and the number is growing. In Asia, some countries, including Japan and Taiwan, have an even higher prevalence of chronic hepatitis infection (Kew 1998).

Alcohol abuse can also cause acute and chronic hepatitis. Alcoholic hepatitis can range from a mild hepatitis, with abnormal laboratory tests being the only indication of disease, to severe liver dysfunction with complications such as jaundice (yellow skin caused by bilirubin retention), hepatic encephalopathy (neurological dysfunction caused by liver failure), ascites (fluid accumulation in the abdomen), bleeding esophageal varices (varicose veins in the esophagus), abnormal blood clotting and coma. Histologically, alcoholic hepatitis has a characteristic appearance with ballooning degeneration of hepatocytes, inflammation with neutrophils and sometimes Mallory bodies (abnormal aggregations of cellular intermediate filament proteins). Alcoholic hepatitis is reversible if the patient stops drinking, but it usually takes several months to resolve. Alcoholic hepatitis can lead to liver scarring and cirrhosis. Chronic alcoholism is the most common cause of cirrhosis in the U.S.; thirteen million Americans suffer from chronic alcoholism and 10-20% of these patients eventually develop liver cirrhosis (Naccarato, R. and F. Farinati (1991)). "Hepatocellular carcinoma, alcohol, and cirrhosis: facts and hypotheses." (*Dig Dis Sci.* 36(8): 1137-42). Although the incidence of liver cancer from alcoholic cirrhosis is lower than from hepatitis cirrhosis, there is a strong association that exist and there are many more people with alcoholic cirrhosis than hepatitis cirrhosis (Seitz, H. K., G. Poschl, and U. A. Simanowski (1998). "Alcohol and Cancer." *Recent Dev. Alcohol* 14:67-95; Naccarato et al. 1991).

Exposure to Chemicals and Toxins

Exposure to certain chemicals and toxins can lead to hepatocellular carcinoma. Perhaps the best known and most extensively studied of these is aflatoxin. Aflatoxin is a poison produced by the mould *Aspergillus Flavus*. Aflatoxin can contaminate stored foods such as peanuts, grains and cassava, especially in tropical areas. Dietary contamination with aflatoxin has been a particular problem in some underdeveloped countries in Africa and Far East Asia. Aflatoxin readily causes liver cancer in laboratory animals and, in man, may potentiate the cancer-causing effects of hepatitis B infection (Ross, R. K., J. M. Yuan, et al. (1992)). "Urinary aflatoxin biomarkers and risk of hepatocellular carcinoma." (*Lancet* 339(8799): 943-6). However, the extent of its role as a cause of hepatocellular carcinoma in humans is not yet fully understood.

Cirrhosis of the Liver

It is believed that chronic liver damage that leads to cirrhosis also predisposes normal hepatocytes to undergo malignant change. Cirrhosis is characterized anatomically by widespread nodules in the liver combined with fibrosis. Cirrhosis of the liver can be defined as the widespread scaring of the liver tissue that, despite the regenerative potential of hepatocytes, results in structural and functional compromise of the liver. Cirrhosis is the end product of a wide variety of liver disorders. In the United States, alcohol abuse is the leading cause of liver cirrhosis. Cirrhosis can result from many causes other than alcohol such as chronic viral hepatitis, metabolic and biliary diseases. The co-existence of another chronic liver disease in a patient who abuses alcohol likely increases the risk of developing cirrhosis (e.g. an alcoholic with chronic viral hepatitis C). Some of the complications of cirrhosis are jaundice, ascites, edema, bleeding esophageal varices, blood coagulation abnormalities, coma and death.

Although, the question of whether alcohol, by itself, causes heptocellular carcinoma has not been fully resolved, it is known that cirrhosis can lead to end-stage liver disease like liver cancer, which often arises in the presence of alcohol cirrhosis. It is not known whether the underlying cirrhosis or the alcohol itself predisposes one to cancer. Alcohol use can increase the risk of hepatocellular carcinoma due to hepatitis B virus, but a similar role in hepatitis C virus-associated hepatocellular carcinoma has not been observed (Shimizu S., K. Kiyosawa, et al. (1992). "High prevalence of antibody to hepaptitis C virus in heavy drinkers with chronic liver diseases in Japan." *J Gastroenterol Hepatol* 7(1):30-5). The role of cirrhosis in hepatocellular carcinogenesis appears to be that of a promoter (Giovannini, M., D. Elias, et al. (2001). "Hepatocellular carcinoma." *Br J Cancer* 84 Suppl 2: 74-7). Whether hepatocellular carcinoma is ever an inevitable consequence of cirrhosis per se is uncertain. Chronic hepatitis B or C infection, alcohol abuse, or both can result in cirrhosis, which regardless of etiology can be complicated by tumor formation. Studies have shown that cirrhotic patients have a 5 to 10% annual risk of developing liver cancer (Aguayo and Patt 2001).

Treatments for Diseases of the Liver

The most common diseases of the liver include hepatitis from alcohol, viral, metastatic and autoimmune etiology, cirrhosis and cancer of the liver. At present time, treatment options are very limited in all cases.

Even with the many advances in medicine and increasing number of treatment options for liver cancer, the prognosis remains poor, and life expectancy remains dismal. Symptomatic hepatocellular carcinoma carries a grave prognosis, largely because of the extent of tumor burden when the diagnosis is made and the presence of coexisting cirrhosis—so much so that the annual mortality rate from the tumor is virtually the same as the annual incidence. From the time of diagnosis, the average life expectancy is less then 1 year, with the majority of people dying within 3 to 6 months (Aguayo and Patt 2001).

Therapeutic options for primary liver cancer can be considered depending on the stage of the hepatocellular cancer, which correlate to three distinct developmental stages of the disease. The first stage occurs prior to the actual diagnosis of cancer. Such first stage therapeutic options are presented to patients having major risk factors. These therapies are generally labeled chemoprevention. The second stage is relevant for patients initially diagnosed with a solitary liver mass with dimensions amenable to resection or transplantation and no evidence of distant disease. These strategies may be considered as potentially curative. The therapeutic options associated with the final stage of the disease arise upon instances where either the primary mass is unresectable, because of its size or location, and/or there is extensive distant disease. Strategies at this stage are confined to palliation.

Chemoprevention Therapy of Liver Cancer

Chemoprevention is the concept of interfering with the metabolism of a carcinogen, preventing it from interacting with nucleophiles (especially DNA), and/or preventing precancerous lesions from progressing to cancer (Okuno, M., S. Kojima, et al. (2001). "Chemoprevention of hepatocellular carcinoma: concept, progress and perspectives." *J Gastroenterol Hepatol* 16(12): 1329-35). Since the major risk factor for liver cancer has been hepatitis induced cirrhosis, much of the chemopreventative efforts have centered on preventing and treating hepatitis infection. Hepatitis B vaccination has had a tremendous impact on infection rate of Hepatitis B in Asia and the U.S. For patients already infected with hepatitis, the only treatment modality that has shown potential benefit in preventing or slowing the development of cirrhosis and liver cancer is interferon injection. Interferon is an anti-viral agent, which has been shown to lower viral load and decrease the amount of liver damage. Progression of chronic hepatitis is followed by measuring viral load (amount of virus in the body) and the amount of liver damage which can be measured by the elevation of liver enzymes—AST and ALT in the blood. The response rate for interferon therapy of chronic hepatitis varies. The overall response rate is roughly 50% (response defined by normalization of liver enzyme levels and reduction of viral load) (Okuno, Kojima et al. 2001). However, approximately half of the responders will have resumption of elevated liver enzymes and viral load once they stop the injections (Okuno, Kojima et al. 2001). The side effects of interferon are severe and can include general malaise, flu-like symptoms, and moderate to severe anemia. Thus, prolonged treatment with interferon is difficult, especially for older patients or others with comorbid conditions. Even healthy individuals find it difficult to maintain prolonged therapy because of the side effects adversely affecting their daily activities (Okuno, Kojima et al. (2001)).

Curative Therapies for Liver Cancer

The only treatment modalities considered as curative are surgical resection of the liver mass and liver transplantation. (Kuyvenhoven, J., C. B. Lamers, et al. (2001). "Practical management of hepatocellular carcinoma." *Scand J Gastroenterol Suppl* 234: 82-7). However, less than 15% of patients with liver cancer are candidates for curative therapy upon diagnosis. Considering that the best survival rates are less than 70% at 5 years with up to 70% recurrence after surgery, curative therapy is really a misnomer (Georgiades, C. S., D. E. Ramsey, et al. (2001). "New nonsurgical therapies in the treatment of hepatocellular carcinoma." *Tech Vasc Interv Radiol* 4(3): 193-9; Giovannini, M., D. Elias, et al. (2001). "Hepatocellular carcinoma." *Br J Cancer* 84 Suppl 2: 74-7).

The mainstay of the curative strategies is partial hepatectomy (removal of part of the liver that houses the tumor). Over the past decade improvement in peri-operative management has resulted in the procedure related mortality of less then 10%, but the actual number varies from institution to institution. Patients with underlying liver cirrhosis have a higher peri-operative mortality rate, as high as 15% (Kuyvenhoven, Lamers et al. 2001). The regenerative capacity of the liver allows for up to two thirds of the liver mass to be resected in patients without preexisting cirrhosis. Again, surgical resection is hampered because the majority of patients with hepatocellular cancer have underlying cirrhosis. Cirrhotic livers present particular challenges to the surgeon, including, difficult surgical dissection, predisposition to excessive bleeding and postoperative liver failure secondary to compromised reserves. Other exclusionary criteria for surgery include a cancer larger than 5 cm, involving both lobes of the liver, straddling the portal vein, and having distant metastatic deposits. The 5-year survival after partial hepatectomy is 30% to 50%. This compares favorably with the dismal 5% survival with non-surgical therapy, but remains an insufficient cure, since greater then half of these patients die within 5 years (Kuyvenhoven, Lamers et al. (2001)). Despite the potential for cure, 80% of partial hepatectomy survivors develop disease recurrence. Despite technical advancement and improved mortality rates, the fact remains that, even after resection, persons diagnosed with primary liver cancer do not have a hopeful prognosis (Kuyvenhoven, Lamers et al. ((2001)).

Theoretically, total hepatectomy with orthotopic liver transplantation (OLT) is the optimum treatment for liver cancer. It provides removal of the primary tumor and the cirrhotic hepatic parenchyma, both of which increase life expectancy. Removing the diseased liver also prevents local recurrence from microscopic tumor disease that may have initiated elsewhere in the liver, distant from the initial tumor. This fact is confirmed through 5 year survival rates of 50-60% after transplantation (Kashef, E. and J. P. Roberts (2001)). "Transplantation for hepatocellular carcinoma." *Semin Oncol* 28(5): 497-502). Due to the very limited number of organ donors available, strict transplant criteria have been established. This ensures that the limited number of donated livers go to the best, most suited host. The average wait period for a liver transplantation is between 6 months to 2 years (Kashef and Roberts (2001)). Many patients die while they are on the wait list or are dropped from the list secondary to tumor growth or spread to other organs. Even after transplantation, tissue rejection and life-long immunosuppression complicates quality of life and longevity. Living-related donors reduce the chances of rejection, however, at a prohibitive cost to the donor. (Kashef and Roberts (2001)).

Palliative Procedures for Liver Cancer

The majority of patients with liver cancers are diagnosed at a stage at which the preventive and curative measures are no longer effective treatment options. Therefore, significant development and research have focused on palliative options. Patients who are not candidates for surgical resection or transplantation can be considered for a variety of minimally invasive procedures that appear to provide mediocre improvement in survival. Such procedures include alcohol, cryogenic or radio-frequency ablation, and chemotherapeutic embolization. Although significant strides have been made for chemotherapeutic regiments for other types of cancer in the last 20 years, these treatments have not made a significant impact on the survival rate among liver cancer patients. It may be stated that the quality of life for patients with unresectable liver cancer rapidly deteriorates. Non-traditional therapies such as vitamins and herbal remedies constitute the remaining balance of therapeutic options. However, these therapies have yet to have a significant impact on survival or proven therapeutic benefit to the patient.

Ablative therapies were developed to shrink tumor mass to improve surgical resectability or as bridging procedure while patients await transplantation. Such procedures include percutaneous ethanol injection, radiofrequency ablation, and transarterial chemoembolization.

Percutaneous ethanol injection (PEI) has been the mainstay of palliative therapy for small or multiple unresectable liver cancers for over two decades. Percutaneous radiology-guided injections of purified ethanol are made into a distinct tumor mass. Ethanol induces tumor cell death through cellular dehydration, microvascular thrombosis, and coagulation necrosis (Barnett, C. C., Jr. and S. A. Curley (2001). "Ablative techniques for hepatocellular carcinoma." *Semin Oncol* 28(5): 487-96). However, utilization of PEI is limited in that it cannot be administered to patients having poor hepatic function, lesions larger than 3 cm or more than 3 lesions (Barnett and Curley 2001). Overall, long term survival remains unaffected Radiofrequency (RF) ablation and cryoablation (CA) are two methods that induce tumor cell death by extreme heat and cold, respectively. RF is accomplished by introducing a probe into the tumor and heating the tumor to a specific temperature, using radiofrequency emissions. CA also employs a probe that causes freezing induced tumor necrosis directly as well as through microvascular thrombosis directly to the tumor site. Again, the primary use for these therapies is as bridging modalities while patients await curative surgery. (Little, S. A. and Y. Fong (2001). "Hepatocellular carcinoma: current surgical management." Semin Oncol 28(5): 474-86) and (Barnett and Curley (2001)). The observed benefit in survival is marginal at best when used alone.

Transarterial chemoembolization (TACE) is performed by fluoroscopically cannulating the major hepatic artery and injecting chemotherapeutic and embolizing agents directly into the vascular territory of the tumor. The preferred result is tumor-targeted chemotherapy and ischemia with resultant tumor necrosis. As with other ablative therapies, the major utility of TACE lies in bridging patient treatment while surgical therapy is awaited. No significant long-term improvement in survival has been noted. (Little and Fong 2001) (Barnett and Curley 2001).

Although the ablative therapies have been shown to shrink the liver tumor in many cases and has been used effectively as bridging therapy for patients awaiting definitive therapy, the use of these ablative techniques alone has not been proven to provide either cure or increased survival for patients with hepatocellular carcinoma. These are all invasive procedures and, accordingly, all have risks associated with anesthesia and general surgical complications such as bleeding and infection. There is also the inherent risk of fulminent liver failure if too large of an area of the liver is ablated. Therefore, these therapies come with significant risk, high costs, and without appreciable long-term benefit.

Despite impressive improvement in survival and many cures with systemic chemotherapy for cancers in general, results of chemotherapies in liver cancer are dismal. Doxorubicin, the only FDA approved agent for liver cancer is effective in less than 20% of patients. However, the median survival rate remains less than 6 months (Leung, T. W. and P. J. Johnson (2001). "Systemic therapy for hepatocellular carcinoma." Semin Oncol 28(5): 514-20). The latest phase m clinical trial showed that the response rate of Doxorubicin to be only 11% with median survival of patients treated with Doxorubicin to be 7 months. Clinical trials are ongoing with many agents either as mono-therapy or poly-therapy including cisplatin, 5-fluorouracil, mitomycin C, gemcitabine and interferon, as well as many others. There is no definitive data to establish any of these trial agents as a standard of care. Although, their efficacy remains to be established, all of these agents have well established significant undesired and deleterious side-effect without an improvement in survival (Leung and Johnson 2001; Treiber, G. (2001). "Systemic treatment of hepatocellular carcinoma." Dig Dis 19(4): 311-23).

Induction of apoptosis, or programmed cell death, in liver cancer cell cultures has prompted investigation of therapeutic effects of Vitamin A (retinoic acid) in patients with liver cancer (Muto, Y., H. Moriwaki, et al. (1996). "Prevention of second primary tumors by an acyclic retinoid, polyprenoic acid, in patients with hepatocellular carcinoma. Hepatoma Prevention Study Group." N Engl J Med 334(24): 1561-7.; Nakamura, N., Y. Shidoji, et al. (1996). "Apoptosis in human hepatoma cell line induced by 4,5-didehydro geranylgeranoic acid (acyclic retinoid) via down-regulation of transforming growth factor-alpha." Biochem Biophys Res Commun 219(1): 100-4). Retinoic acid can exist in multiple, sometimes interchangeable isomeric states (i.e. cis and trans). Clinical studies with beta-all trans retinoic acid failed to demonstrate any benefit despite promising experimental data (Meyskens, F. L., Jr., J. Jacobson, et al. (1998). "Phase II trial of oral beta-all trans-retinoic acid in hepatocellular carcinoma (SWOG 9157)." Invest New Drugs 16(2): 171-3). Other forms of retinoic acid are being investigated in clinical studies.

Other vitamins are being investigated for their potential therapeutic effects. For example, Vitamin E supplements have been shown to reduce liver damage in patients with chronic Hepatitis B. In a study in rats, Vitamin C and Vitamin K have been shown to have synergistic apoptosis-inducing actions in hepatocellular carcinoma in rats (Sakagami, H., K. Satoh, et al. (2000). "Apoptosis-inducing activity of vitamin C and vitamin K." Cell Mol Biol (Nois-le-gand) 46(1): 129-43). Vitamin C and Aloe Vera supplements have been shown to reduce the severity of chemical hepatocarcinogenesis (Shamaan, N. A., K. A. Kadir, et al. (1998). "Vitamin C and aloe vera supplementation protects from chemical hepatocarcinogenesis in the rat." Nutrition 14(11-12): 846-52).

Herbal remedies have been investigated as starting points in an attempt to extract possible biologically active agents for myriad pharmacotherapies. Cancer therapy is no exception, with many current products used to combat cancer originally derived from various herbs and plants. Currently, there are countless claims of herbal products with anti-cancer effects. However, only the few that have had published anti-cancer data will be discussed. Indeed, the research involving "natural" remedies discussed herein, has involved primarily animal models and cell lines. In the few studies performed in humans, none present imaging, laboratory data, or other evidence to support their claims. Moreover, there are no conclusive studies for any of these products.

The herbal medicine "Sho-saiko-to" (TJ9) (a mixture of 7 herbs: bupleurum root, pinellia tuber, scutellaria root, jujube fruit, ginseng roots, glycyrrhiza root, and ginger rhizome) has been reported to inhibit liver cancer development (hepatocarcinogenesis) and proliferation in certain liver cancer cell lines and in rat models (Sakaida, I., Y. Matsumura, et al. (1998). "Herbal medicine Sho-saiko-to (TJ-9) prevents liver fibrosis and enzyme-altered lesions in rat liver cirrhosis induced by a choline-deficient L-amino acid-defined diet." J Hepatol 28(2): 298-306).

Paeoniae Radix (PR) is the root of the traditional Chinese Herb called Paenoniae lactiflora Pallas, which has been commonly used to treat liver cancer in China for centuries. Several early studies have shown that extracts of PR have some anti-cancer growth activities. One study has shown that there is evidence that PR extract can induce programmed cell death (apoptosis) in two human hepatoma cells lines (Lee, S. M., M. L. Li, et al. (2002). "Paeoniae Radix, a Chinese herbal extract, inhibit hepatoma cells growth by inducing apoptosis in a p53 independent pathway." Life Sci 71(19): 2267-77).

Lemon grass (Cymbopogon citrates, Stapf) extracts have been shown to inhibit hepatocarcinogenesis in rats. Therefore, it is implicated as a possible chemopreventive agent (Puatanachokchai, R., H. Kishida, et al. (2002). "Inhibitory effects of lemon grass (Cymbopogon citratus, Stapf) extract on the early phase of hepatocarcinogenesis after initiation with diethylnitrosamine in male Fischer 344 rats." Cancer Lett 183(1): 9-15).

Aloe-emodin is a compound present in traditional medicinal plants like Rhei Rhizoma and Aloe Vera. Several studies have shown that aloe-emodin may induce two separate apoptotic pathways in two human hepatoma cells lines. It is being investigated as a possible chemopreventative agent (Lee, K. Y., J. H. Park, et al. (1997). "Aloesin up-regulates cyclin E/CDK2 kinase activity via inducing the protein levels of cyclin E, CDK2, and CDC25A in SK-HEP-1 cells." Biochemistry & Molecular Biology International 41(2): 285-92; Corsi, M. M., A. A. Bertelli, et al. (1998). "The therapeutic potential of Aloe Vera in tumor-bearing rats." *International Journal of Tissue Reactions* 20(4): 115-8; Kuo, P. L., T. C. Lin, et al. (2002). "The antiproliferative activity of aloe-emodin is through p53-dependent and p21-dependent apoptotic pathway in human hepatoma cell lines." *Life Sciences* 71(16): 1879-92).

The herbal/Japanese medicine SNMC (Stronger Neo-Minophagen C), whose active component is glycyrrhizin (a saponin extracted from licorice) has been utilized to improve the liver function in China and Japan. Preliminary data suggest it is effective in helping to, prevent hepatocarcinogenesis in patients with Hep B/C with cirrhosis (Arase, Y., K. Ikeda, et al. (1997). "The long term efficacy of glycyrrhizin in chronic hepatitis C patients." *Cancer* 79(8): 1494-500).

One study reports that pu tuo ointment and herbs when applied as an ointment and taken orally can improve survival in patients with primary liver cancer (Wang, D. L. (1990). "[Analysis of 70 cases of primary liver carcinoma treated by pu tro ointment and herbs]." *Zhong Xi Yi Jie He Za Zhi* 10(12): 723-5, 708).

AHCC (Active Hexose Correlated Compound), an extract obtained from several kinds of basidiomycetes (Chinese mushrooms) has been shown to improve survival and reduce recurrence in patient after resection of hepatocellular carcinoma (Thatte, U., S. Bagadey, et al. (2000). "Modulation of programmed cell death by medicinal plants." *Cell Mol Biol (Noisy-le-grand)* 46(1): 199-214).

Dietary carotenoid-rich extracts from carrots, tomatoes, and orange juice have been shown in rat models to substantially inhibit biochemical and cellular events thought to play a role in early stages of hepatocarcinogenesis (He, Y., M. M. Root, et al. (1997). "Effects of carotenoid-rich food extracts on the development of preneoplastic lesions in rat liver and on in vivo and in vitro antioxidant status." *Nutr Cancer* 27(3): 238-44).

Epidemiological studies give evidence that cruciferous vegetables (CF), including broccoli and broccoli extracts, protect humans against cancer. Results from animal experiments show a reduction in chemically induced tumor formation (Zhang, Y., P. Talalay, et al. (1992). "A major inducer of anticarcinogenic protective enzymes from broccoli: isolation and elucidation of structure." *Proc Natl Acad Sci USA* 89(6): 2399-403).

BRIEF DESCRIPTION OF THE DRAWINGS

Brief Description of FIGS. 1-7

FIG. 1

A drawing depicting the gross anatomical location of the liver in the abdominal cavity. This illustrates the liver's relative location in relation to the diaphragm, intestine, gallbladder, and stomach.

FIG. 2

This figure summarizes the malignant changes in the cells during the process of carcinogenesis.

FIG. 3

This graph represents the trend in liver enzyme levels (AST and ALT) for a 68 year old Asian male patient discussed in example 1. The graph tracks AST and ALT levels (normal levels: ALT-0 to 40, AST-0 to 60) on the y-axis versus time on the x-axis. The data points are laboratory tested levels measured between February, 2002 and December, 2002.

FIG. 4

This graph represents the trend in the tumor marker AFP for a 68 year old Asian male patient discussed in example 1. The graph tracks AFP level (normal levels-0 to 7) on the y-axis versus time on the x-axis. The data points are laboratory tested levels measured between February, 2002 and December, 2002.

FIG. 5

This is a magnetic resonance image (MRI of the liver of 68 year old Asian male patient discussed in example 1 of February, 2002. The outline within the liver represents the area of tumor within the liver.

FIG. 6

This is a CT scan of the liver of 68 year old Asian male patient discussed in example 1 of April, 2002. The outline within the liver represents the area of tumor within the liver. This illustrates the significant tumor size reduction after oral administration of the composition daily for 1 month. This represents a tumor volume reduction of greater than 60% as compared to the MRI of February 2002 (See FIG. 5).

FIG. 7

This is a CT scan of the liver of 68 year old Asian male patient discussed in example 1 taken in November 2002. The outline within the liver represents the area of tumor within the liver. This illustrates the continued dramatic reduction after patient continues oral administration of composition with no other treatment modalities. This represents a tumor volume reduction of greater than 80% as compared to the MRI of February 2002 (See FIG. 5).

SUMMARY OF THE INVENTION

The invention described herein includes new compositions that can be derived from vegetables and herbs for use as a therapy for the treatment of liver cancer, hepatitis, and cirrhosis, as well as other forms of liver diseases. The compositions of this invention can also be used as a dietary supplement to aide in normal physiological bodily functions and for use in the prevention of liver cancer as well as other forms of cancer. The compositions of this invention can be obtained from a combination of vegetables and other natural ingredients, including: *Brassica oleracea, Daucus carota, Apium graveolens* L., *Petroselinum crispum, Spinacia oleracea* L, *Lycopersicon esculentum, Citrullus vulgaris, Citrus aurantifolia, Cymbopogon* sp., *Beta vulgaris*, aloe vera, and honey. The compositions may also be obtained from a combination of *Brassica oleracea, Daucus carota, Apium graveolens* L., *Petroselinum crispum, Spinacia oleracea* L, *Beta vulgaris*, aloe vera, and honey. In addition, the compositions can be obtained from a combination of *Brassica oleracea, Daucus carota, Apium graveolens* L., *Petroselinum crispum, Spinacia oleracea* L, *Beta vulgaris*, aloe vera, and honey. Compositions from these and other combinations and subcombinations of these ingredients are contemplated. The compositions of this invention may be administered orally or by any other means known to those of skill in the art, and as otherwise described.

The object, advantages, and features of the invention will be further apparent from the following detailed description of embodiments of the invention, and the examples described herein.

DETAILED DESCRIPTION OF THE INVENTION AND THE PREFERRED EMBODIMENT

The Compositions

The compositions of this invention may comprise one or more of the following vegetables, or extracts of those vegetables: *Brassica oleracea, Daucus carota, Apium graveolens* L., *Petroselinum crispum, Spinacia oteracea* L, *Beta* vulgaris. In addition, one or more of the following organic ingredients may also be added to the composition: aloe vera, and honey. Furthermore, a composition of this invention is contemplated that contains *Spinacia oleracea, Brassica oleracea* and *Daucus carota*. The composition described herein can comprise the juice extract of the vegetable described, where such juice extract may be combined with other juice extracts or ingredients into a composite liquid. In addition, the composition may be derived from the combination of the individual ingredients after the juice extract of each ingredient has been desiccated. In still another embodiment, the composite liquid described above may also be desiccated to form a dry form of the composition. Such dry forms of the composition may be administered in dry form, e.g., in capsules or pills, or other forms; or, the dry form may be mixed with water, or any other liquid, and administered. Such dry forms of the composition may also be mixed with a pharmaceutically acceptable carrier. In addition, the active ingredients of said composition may be purified and, if desired, mixed with a pharmaceutically acceptable carrier. Also, the composite liquid can also be administered to the patient intravenously in a purified form or soluble form.

In one example of such a composition, for each 30 oz. of the composition in liquid form, the composition comprising:

32.78±15%, *Apium graveolens* L. 24.59±12%, *Petroselinum crispum* <1±0.5%, *Spinacia oleracea* L 11.47±5%, *Beta vulgaris* 8.19±4%, aloe vera <1±0.5%, and honey <1±0.5%. The composition may comprise 22.95% *Brassica oleracea* ±15%, ±12.5%, ±10%, ±5%, ±2.5%. The composition may comprise 32.78% *Daucus carota* ±25%, ±20%, ±15%, ±12.5%, ±10%, ±5%, ±2.5%. The composition may comprise 24.59% *Apium graveolens* L. ±20%, ±15%, ±12.5%, ±10%, ±5%, ±2.5%. The composition may comprise 1% *Petroselinum crispum* ±0.8%, ±0.5%, ±0.25%, ±0.10%. The composition may comprise 11.47% *Spinacia oleracea* L ±10%, ±8%, ±5%, ±2.5%, ±1%. The composition may comprise 8.19% *Beta vulgaris* ±6%, ±4%, ±2%, ±1%. The composition may comprise 1% aloe vera ±0.5%, ±0.25%. The composition may comprise 1% honey ±0.5%, ±0.25%. If is further contemplated that the composition may comprise a smaller grouping of the following ingredients (or their respective active ingredients): *Brassica oleracea, Daucus carota, Apium graveolens* L., *Petroselinum crispum, Spinacia oleracea* L, *Beta vulgaris*, aloe vera and honey.

The composition of this invention may be used as a dietary supplement and/or anticancer agent. The composition may comprise either the above listed ingredients, its active compounds, or said ingredients and active compounds plus one or

TABLE I

|  | Brassica oleracea | Apium graveolens | Spinacia oleracea | Daucus carota | Beta vulgaris | Petroselinum crispum | Honey | Aloe Vera* |
|---|---|---|---|---|---|---|---|---|
| Calories | 86.42 | 55.38 | 37.1 | 193.7 | 49.58 | 4.26 | 64 |  |
| Protein (g) | 9.64 | 4.26 | 5.30 | 7.45 | 1.34 | 0 | 0 |  |
| Carbohydrates (g) | 19.28 | 12.78 | 5.30 | 45.7 | 10.72 | 0 | 17 |  |
| Fiber (g) | — | 4.26 | 5.30 | 14.9 | 2.68 | 0 | 0 |  |
| Calcium (mg) | 144.6 | 136.3 | 159.0 | 119.2 | 18.76 | 21.3 | 1 |  |
| Iron (mg) | — | 0 | 5.30 | 0 | 1.34 | 0 | 0 |  |
| Magnesium (mg) | 77.12 | 38.34 | 127.2 | 67.05 | 26.80 | 8.52 | 0 |  |
| Phosphorus (mg) | 212.08 | 85.2 | 79.5 | 201.15 | 42.88 | 8.52 | 1 |  |
| Potassium (mg) | 1031.48 | 979.8 | 885.1 | 1043 | 347.06 | 89.46 | 11 |  |
| Sodium (mg) | 86.76 | 298.2 | 127.20 | 156.45 | 84.1 | 8.52 | 1 |  |
| Selenium (mg) | 9.64 | 0 | 0 | 7.45 | 1.146 | 0 | 0 |  |
| Vitamin C (mg) | 289.2 | 25.56 | 42.4 | 44.7 | 4.02 | 21.3 | 0 |  |
| Thiamin (mg) | 0 | 0 | 0 | 0.745 | 0 | 0 | 0 |  |
| Riboflavin (mg) | 0 | 0 | 530 | 0 | 0 | 0 | 0 |  |
| Niacin (mg) | 0 | 0 | 0 | 7.45 | 0 | 0 | 0 |  |
| Vitamin B6 (μg) | 0 | 0.426 | 0.530 | 0.745 | 0.134 | 0 | 0 |  |
| Folate (μg) | 221.72 | 93.72 | 307.4 | 67.05 | 91.12 | 25.56 | 0 |  |
| Vitamin A (IU) | 9543.6 | 455.8 | 10680 | 127835 | 40.2 | 843.48 | 0 |  |
| Vitamin A (RE) | 954.36 | 42.6 | 1071 | 12784 | 4.02 | 85.2 | 0 |  |
| Vitamin E (mg) | 0 | 0 | 5.30 | 0 | 0 | 0 | 0 |  |
| Vitamin K (μg) | 652 | 40.91 | 636.36 | 22.73 | 3.4 | 92.02 | — |  |

Photochemical Content

| | Carotenoids (μg) | | | | | Other Photochemicals | | |
|---|---|---|---|---|---|---|---|---|
| | Alpha-Carotene | Beta Carotene | Beta-cryptoxanthin | Lutein & zeaxanthin | Lycopene | Lignans | Indoles | Isothiocyanates |
| *Beta vulgaris* | | 2560 | | | | | | |
| *Brassica oleracea* | 1 | 779 | 0 | 2445 | 0 | X | X | X |
| *Daucus carota* | 4425 | 7275 | 0 | 358 | 0 | X | | |
| *Apium graveolens* L | 0 | 150 | 0 | 232 | 0 | | | |
| *Petroselinum crispum* | 0 | 0 | 0 | 0 | 0 | | | |
| *Spinacia oleracea* L. | 0 | 5597 | 0 | 11938 | 0 | | | |

*Aloe vera and extracts of aloe vera comprise the following compounds:
Anthraquinones (aloin, aloe-emodin), resin, tannins, polysaccharides, aloectin B
**Brassica oleracea and extracts of brassica oleracea comprise the following photochemical elements: lignans, indoles, isothiocyanates Preferably, the composition comprises the following ingredients: *Brassica oleracea* 22.95±11%, *Daucus carota* more pharmaceutically acceptable carriers. In addition to the compounds listed above, methods of determining active ingredients and screening for activity in the compositions of this invention can be carried out according to methods known to those of skill in the art, and according to methods described in the examples herein. Compositions of this invention may be mixed with pharmaceutically acceptable carriers or excipients known to those of skill in the art, and administered according to methods known to those of skill in the art including:

i.) Oral Administration in the form of juice, powders, tablets, suspension, emulsifiers, capsules, granules, troches, pills, suspensions, spirits, syrups, and limonades;

ii) Injectable Administration intravenously or otherwise;

iii) Topical Administration in the form of ointments, solids, suspensions, powders, paps, suppositories, aerosols, cataplasmas, liniments, lotions, enemas, and emulsifiers.

In addition, well-known excipients in the form of solid or liquid may be used. As mentioned above, the formulation should contain the active ingredients, including but not limited to *Brassica oleracea, Apium graveolens, Spinacia, Daucus carota, Beta vulgaris, Petroselitium crisaum*, aloe vera, retinoids, vitamin K, and asorbic acid, of this invention. The several examples of excipients used to administer the dosage forms are as follows:

Excipients in powders and other oral powders: lactose, crystalline cellulose, starch, dextrin, calcium phosphate, calcium carbonate, synthetic and natural aluminum dioxide, magnesium oxide, dried aluminum hydroxide, magnesium stearate, and sodium bicarbonate;

Excipients in topical powders: zinc oxide, talc, starch, kaolin, borate powder, zinc stearate, magnesium stearate, magnesium carbonate, precipitated calcium carbonate, bismuth subgallate, and potassium aluminum sulfate powder;

Excipients in liquids: water, glycerin, propylene glycol, sweet-taste syrup, ethanol, fatty oil, ethylene glycol, polyethylene glycol, and sorbitol;

Excipients in ointments: hydrophobic or hydrophilic base (including oil-soluble base, water-soluble base and suspended base) prepared by mixing fat, fatty oil, lanoline, Vaseline, glycerin wax, Japan wax, paraffin, paraffin sulphate, resins, higher alcohols, plastics, glycols, water, or surfactant.

It is contemplated that the composition can be administered in any of the forms considered herein, or otherwise known to those of skill in the art. Preferably, the composition is administered orally in a liquid form, either as an extract, concentrated extract or other liquid form. Most preferably, the composition is administered orally twice a day, three times a day, or four times a day, with each dosing varying between 5 oz-20 oz. depending on the person's state of health, weight, severity of disease, response of disease, and overall liver function.

The composition may be administered as a dietary supplement to facilitate normal physiological function and growth.

The composition, when taken at an effective dose over a period of time, may reduce or eliminate the tumor burden in liver cancer.

The composition, when taken at an effective dose over a period of time, may aid and expedite liver regeneration.

The composition when taken at an effective dose over a period of time, prevents development of liver cancer in predisposed patients with liver cirrhosis.

The composition when taken at an effective dose over a period of time, prevents development of liver cancer in predisposed patients with viral and non-viral hepatitis.

The composition, when taken at an effective dose over a period of time, may be effective in treating viral hepatitis by lowering the liver enzymes AST and ALT and lowering the viral hepatitis load found in the body.

The composition and its methods of use disclosed herein may be used in combination with other known, standard or experimental treatment protocols for liver cancer.

The composition and its methods of use disclosed herein may be used as bridging therapy to down-grade the size of inoperable liver cancers to a resectable or transplantable size.

The composition and its methods of use disclosed herein may be used to aid in liver regeneration for normal liver parenchyma damaged in hepatic chemoembolization.

The composition and its methods of use disclosed herein may be used for treatment of other disorders of the hepatobiliary system.

The composition and its methods of use disclosed herein may be used in combination with other known, standard or experimental treatment protocols for other cancers.

The composition and its methods of use disclosed herein may be used in combination with other known, standard or experimental preventative protocols for liver and other cancers.

Clinical Results

Due to the nontoxic nature and excellent side-effect profile, this therapeutic treatment can be performed as an outpatient treatment with no need for hospitalization, frequent laboratory tests, or additional medication to treat ill side-effects. The patient would only need to see a physician every few weeks to months for radiographic and laboratory follow-up evaluations.

In the case of treatment for liver or other forms of cancer, hepatitis and/or cirrhosis, the results may be seen as early as 3-4 weeks after treatment. One of skill in the art would be aware of methods that can be used to evaluate a patient's response, for example, CT scan, MRI, or by any improvement in overall health. Depending on the patient's symptoms, indications of response and benefits of treatment may include:

a.) Decreased or normalization of Alpha Feto Protein (AFP) level or other tumor markers;

b.) Some shrinkage of the tumor in size of primary and/or metastatic tumor as seen on CT, MRI, or ultrasound or other method of measurement;

c.) Decreased rate of weight loss, or weight gain;

d.) Increase or resumption of normal activity and/or energy level;

e.) Slowing the progression of the symptoms of liver cancer;

f.) Reduction in the rate of tumor expansion;

g.) Lowering of Hepatitis Viral Load in the blood;

h.) Slowing and/or halting the progression of liver damage from cirrhosis;

i.) Delaying or preventing the development of HCC in patients with hepatitis and/or cirrhosis;

j.) Prolong survival time for patients with end-stage HCC;

In the case of chemoprevention, the therapeutic benefit to the patient includes the prevention of, decrease in the likelihood of, and/or reversing the development of carcinogenesis in the liver or other organs in patients with or without hepatitis, and/or with or without cirrhosis.

EXAMPLES

Example 1

68 year old Asian male with long-standing hepatitis C and liver cirrhosis presented to his primary care physician with weight loss, generalized fatigue, loss of appetite and abdominal discomfort. CT scan and MRI showed a large heterogenous lesion of the liver that encompassed 90% of the right lobe of the liver with portal vein invasion/compression as well as multiple small lesions in both lobes of the lung (see FIG. 5). His Alpha-Feto-Protein (AFP) level was 224 (normal range 0-7) (See FIG. 4). CT guided biopsy of the lesion confirmed a diagnosis of hepatocellularcarcinoma. The final diagnosis was end-stage hepatocellular carcinoma with metastasis to both lungs. The lesion was too big for radiofrequency ablation, PEI injection, chemoembolization, surgical resection, or transplantation. In addition, the patient did not tolerate prior treatment with interferon for Hepatitis C and cirrhosis. Given the amount of tumor as well as metastasis to lungs, treatment options were limited to only palliative chemotherapy. Estimated time of survival for this patient was less then 3 months.

The patient did not pursue chemotherapy due to the undesirable side-effects associated with the treatment and the fact that treatment with chemotherapy did not offer a possible cure.

The patient began oral consumption of 10 oz of the composition in Table I in liquid form twice a day. The patient took no other treatment or medication during this time. After one month, the patient's repeat CT scan showed a greater than 50% reduction in size (see FIG. 6). The patient's AFP level went down to 24 (see FIG. 4). Clinically, the patient regained 10 lbs. of the original weight lost (20 lbs) and his activity level returned to normal. Treatment with said composition continued while undergoing bimonthly AFP testing and monthly CT scan of abdomen and chest. The subsequent AFP levels normalized to <7 IU. The subsequent scans showed continued tumor regression of the liver lesion to last measurement of 3×3×4 cm (see FIG. 7), and importantly, the portal vein re-opened. Furthermore, 12 of the 13 lung lesions disappeared. After 12 weeks of treatment with the composition, the patient regained the 20 lbs. he had previously lost and gained an additional 5 lbs. After 10 months of treatment with the composition, the patient's quality of life is excellent. He has resumed daily physical exercise, including walking and swimming. He is able to travel abroad and enjoy life. There have been no ill side-effects noted.

Example 2

A 69 year old male diagnosed with hepatobiliary carcinoma of the liver. He underwent resection but two years later had recurrence. The patient underwent 3 months of systemic chemotherapy but had continued tumor growth. After completion of his chemotherapy regimen, he began taking orally, twice daily, 10 oz. doses of the composition in the liquid extract form. Prior to treatment with the composition, the CT scan showed four lesions in the liver, ranging from 1 cm to 4 cm. After one month of treatment with the composition, repeat CT scan showed that two of the lesions had disappeared completely while the two remaining lesions decreased in size by more than 50% as compared to the previous scan. 6 months post-initiation of treatment, the patient continues to be clinically well. During this 6-month treatment with the composition, patient did not pursue any other forms of treatment.

Example 3

Non-human Data

Individual extracts of *Brassica oleracea* and *Spinacia oleracea* were tested to assess their ability to stop the proliferation of liver cancer cells in vitro (HepG2 cells). HepG2 cell lines are human liver cancer cell lines that are grown in William Media E (standard growth medium) and maintained at 37 degrees Celsius (optimal growth temperature) in a 5% $CO_2$ incubator. Both extracts showed potent inhibitory activity on HepG2 cell growth in a dose dependent manner. *Brassica oleracea* demonstrated an EC50 of 112.74±4.5 mg/mL and *Spinacia oleracea* demonstrated an EC50 of 42.51±1.68 mg/mL. EC50 is the median effective dosing which inhibited proliferation by >50%. Thus, the lower the EC50, the more inhibitory effect the extract had. A composition comprising ingredients having an EC50 value of less than 115, less than 100, less than 75 or less than 50 is further contemplated and may include, for example: *Brassica oleracea, Daucus carota, Apium graveolens, Petroselinum crispum, Spinacia oleracea, Beta vulgaris*, aloe vera, honey, *Lycopersicon esculentum, Citrullus vulgaris, Citrus aurantifolia* and *Cymbopogon* sp. Furthermore, such composition may comprise *Brassica oleracea* and *Spinacia oleracea*.

Individual extracts of *Brassica oleracea, Daucus carota, Apium graveolens* and *Spinacia oleracea* were similarly tested to evaluate for their antioxidant activity. The total antioxidant activity was tested for each extract using the TOSC (total oxyradical assay scavenging capacity) assay. *Brassica oleracea, Daucus carota, Spinacia oleracea*, and *Apium graveolens* had total antioxidant activity levels of 44.03+1.87, 42.56+1.04, 42.2+0.71, 5.08+0.33 μmol of vitamin C equivalent/g of sample, respectively. Antioxidant activity levels have been shown to correspond directly with cancer prevention and anti-cancer activity. Compositions of the invention are contemplated that comprise ingredients having antioxidant levels of more than 40 are further contemplated and may include, for example, *Brassica oleracea, Daucus carota* and *Spinacia oleracea*. Such compositions may also comprise *Petroselinum crispum, Beta vulgaris*, aloe vera, honey, *Lycopersicon esculentum, Citrullus vulgaris, Citrus aurantifolia* and *Cymbopogon* sp.

All above experiments were done in triplicate.

Mechanisms of Action

The documented clinical and radiographic evidence in the patients described, demonstrate that administration of the compositions of the invention causes one or more of the following benefits to a patient suffering from liver cancer and associated disease of the liver, including:

Marked tumor volume reduction at primary tumor site;
Promotion of active liver regeneration (areas of previous tumor were replaced with normal appearing liver, no scar on CT scan);
Normalization of tumor marker AFP levels;
Marked tumor volume reduction at secondary tumor sites;
Decrease in liver function enzymes (AST/ALT);
Reversal of weight loss associated with disease;
Resumption of normal activity;
Improvement in overall quality of life;
Improvement in overall health and well-being;
No ill-side effects;
Marked increase in life-expectancy.

The precise molecular mechanisms associated with the therapeutic benefit that result from the administration of the invention described herein are most likely caused by a synergistic effect of the active ingredients leading to necrosis and apoptosis of the malignant tissues. The probable mechanisms of action are based on an extrapolation of clinical, laboratory, radiographic data seen in the patients described in Examples I and II, and the combination of multiple basic science research papers on the effect of the individual active ingredients of the composition.

It is clear that tumor cell death can be induced directly by apoptosis, necrosis, or a combination of both pathways. AFP level normalization is a direct result of decrease in the number of tumor cells that secrete AFP. In addition, the clinical improvement of weight gain, activity level, and quality of life confirms an overall reduction in the tumor load. The decrease in the volume of tumor size in secondary sites also indicates that the beneficiary effects are spread hematogeously.

The following are examples of mechanisms of anticancer and preventative actions that are thought to be associated with some of the active compounds of the composition. These are only examples of the possible mechanisms of action and are not meant to limit the invention.

Example 1

The retinoids are derivatives of vitamin A. They have diverse structures, pharmacological profiles, receptor affinities, and biologic activities. Experimental animal models, cellular models, epidemiologic data and clinical trials provide a strong rationale for the use of retinoids in cancer therapy and prevention. Vitamin A deficiency in experimental animals has been associated with a higher incidence of cancer and with increased susceptibility to chemical carcinogens (Dragnev, K. H., J. R. Rigas, et al. (2000). "The retinoids and cancer prevention mechanisms." *Oncologist* 5(5): 361-8).

Basic scientific studies have highlighted key regulators of the retinoid signaling pathway. Retinoids signal cellular effects through nuclear retinoid receptors and their coregulators, which leads to ligand-dependent transcriptional activation of target genes and ultimately signals retinoid growth and differentiation effects.

Retinoids bind their nuclear receptors through ligand-binding domains that recognize specific sequences present in genomic DNA. As a result of these ligand-receptor and receptor-DNA interactions, direct retinoid-targeted genes containing retinoid response elements in their promoter regions become transcriptionally activated or repressed. This ultimately leads to changes in gene expression that mediates biological effects. Retinoid-mediated biological signals depend on the type of cells studied and the presence or absence of retinoid receptors. There are two classes of retinoid receptors: retinoic acid receptors (RAR) and retinoid X receptors (RXR) (Dragnev, Rigas et al. (2000)). Each affects separate pathways that have been shown to direct effect on AP-1, a key regulator of cell growth and differentiation. Suzui et al. found that acyclic retinoids inhibit the growth of three hepatoma cell lines which is associated with induction of p21 (a key regulator of apoptosis) and inhibition of cyclin D1 (a key regulator of cell cycle) (Suzui M, M. Masudo, et al. (2002)). "Growth inhibition of hepatoma cells by acyclic retinoid is associated with induction of p21(CIP1) and inhibition of cyclin D1." *Cancer Res* 62(14):3997-4006). Another retinoid, fenrentinide (4HPR), has been shown to induce apoptosis via receptor-independent mechanisms. It is believed that via receptor and non-receptor mediated pathways that retinoids induce tumor cell death (Dragnev, Rigas et al. (2000)).

The in vitro chemopreventive activity of retinoids in certain cell lines has been linked to the triggering of G1 cell cycle arrest, concomitant growth suppression, and a decline in expression of G1 cyclin proteins. This retinoid-triggered G1 arrest is due to a post-translational mechanism. This finding of retinoid-mediated cyclin D1 proteolysis indicates that proteosome-dependent degradation mechanisms are active in the prevention of cellular transformation by retinoids. The delay at G1 by retinoid treatment permits repair of mutagenic damage to genomic DNA by carcinogens (Dragnev, Rigas et al. (2000)).

He et al. tested the effects of carotenoid-rich food extracts on development of preneoplastic lesions in rat liver (He, Y., M. M. Root, et al. (1997). "Effects of carotenoid-rich food extracts on the development of preneoplastic lesions in rat liver and on in vivo and in vitro antioxidant status." *Nutr Cancer* 27(3): 238-44). The carotenoid-rich extracts were found to substantially inhibit biochemical and cellular events involved in early stages of hepatocarcinogenesis (He, Root et al. 1997). In addition, Rieder et al. showed that carcinogenesis and death caused by diethylnitrosamine-induced hepatomas in Sprague Dawley rats can be significantly delayed by feeding only carrots for several days a week (Reider A, M. Adamek, and H. Warba (1983). "Delay of diethylnitrosamine-induced hepatoma in rats by carrot feeding." *Oncology* 40(2):120-3).

In a randomized, double-blinded controlled study, Muto et al. tested whether an acyclic retinoid reduced the incidence of recurrent and second primary hepatomas after surgical resection. Eighty-nine patients were randomized to be treated with retinoid and placebo. They found that the treated group had a significantly lower incidence of recurrent or new hepatoma— 27% vs 49% (P=0.04) (Muto, Y., H. Moriwaki, et al. (1996). "Prevention of second primary tumors by an acyclic retinoid, polyprenoic acid, in patients with hepatocellular carcinoma. Hepatoma Prevention Study Group." *N Engl J Med* 334(24): 1561-7).

Example 2

Aloe-emodin is an anthraquinone that is a major constituent of the aloe vera plant. The aloe vera plant has been shown to have many medically beneficial effects, especially in areas of wound and burn healing. Kuo et al. studied the effect of aloe-emodin on two human hepatoma cell lines (Kuo, P. L., T. C. Lin, et al. (2002). "The antiproliferative activity of aloe-emodin is through p53-dependent and p21-dependent apoptotic pathway in human hepatoma cell lines." *Life Sciences* 71(16): 1879-92). They determined that aloe-emodin induced apoptosis through the p53-dependent pathway in two human hepatoma cell lines (Kuo et al. 2002).

The tumor suppressor gene p53 is an important molecule in the process of apoptosis. Once p53 is activated, the outcome of cellular response is either cell cycle arrest or apoptosis. p53 activates downstream effectors like p21/WAF1 protein that contribute to the arrest of cell in G1 phase by inhibition of cyclin-cdk complex. Activation of p53 also leads to transcriptional transactivation of many other apoptotic genes, including Fas/APO1, Bax, IGF-BP3 and PIG3. Moreover, the level of anti-apoptotic factor Bcl-2, is decreased by p53. Therefore, these actions of p53 commit the cell to apoptosis (Kuo et al. 2002).

Corsi et al. also demonstrated that aloe vera had potential anticancer effects against AH-130 hepatoma cells in rats (Corsi, M. M., A. A. Bertelli, et al. (1998). "The therapeutic potential of Aloe Vera in tumor-bearing rats." *International Journal of Tissue Reactions* 20(4): 115-8). Shamaan et al. investigated the effects of aloe vera in conjunction with vitamin C on induced hepatocarcinogenesis in rats. They found that the combination of vitamin C and aloe vera was able to reduce the severity of chemical hepatocarcinogenesis Shamaan, N. A., K. A. Kadir, et al. (1998). "Vitamin C and aloe vera supplementation protects from chemical hepatocarcinogenesis in the rat." *Nutrition* 14(11-12): 846-52).

Example 3

Vitamin K is a generic term for compounds that include phylloqinone (VK1), menaquinolies series (VK2), and menadione (VK3). Physiologically, the natural K vitamins, VK1 and VK2, are known to act as cofactors for γ-carboxylation of selected glutamates in the N-termini of prothrombin and other VK-dependent coagulation factors. Hepatocellular carcinoma or heptoma cells have impaired ability to perform vitamin K-dependent carboxylation reactions. Therefore patients with hepatomas produce under-carboxylated or immature prothrombin (des-γ-carboxy prothrombin) that is secreted into the plasma. Des-γ-carboxy prothrombin has been found to be one of the most reliable markers for hepatoma (Nishikawa, Y., B. I. Carr, et al. (1995). "Growth inhibition of hepatoma cells induced by vitamin K and its analogs." *J Biol Chem* 270(47): 28304-10; Nishikawa, Y., Z. Wang, et al. (1999). "Inhibition of hepatoma cell growth in vitro by arylating and non-arylating K vitamin analogs. Significance of protein tyrosine phosphatase inhibition." *J Biol Chem* 274(49): 34803-10).

Administration of vitamin K has been shown to inhibit tumor cell growth through the induction of apoptosis and necrosis in human hepatoma cell lines. Nishikawa et al. found that Vitamin K analogs inhibit tumor cell growth by inhibiting the activity of protein-tyrosine phosphatase (PTPase) and activation of ERK1/2 transcription factors (Nishikawa et al. (1995); Nichikawa et al. (1999). PTPase has been demonstrated as a positive regulator of cell growth in tumors and dephosphorylates Endothelial Growth Factor Receptor (EGFR). Increased level of phosphorylated EGFR has been shown to inhibit cellular growth activities in hepatoma cells. Persistent activation of ERK induces cell cycle arrest (Carr, B. I., Z. Wang, et al. (2002). "K vitamins, PTP antagonism, and cell growth arrest." *J Cell Physiol* 193(3): 263-74.; Nishikawa, Carr et al. 1995; Nishikawa, Wang et al. 1999).

Animal studies have shown that rats injected with vitamin K analog demonstrated significant hepatoma growth inhibition (Nishikawa et al. 1998).

Example 4

Vitamin C shows both reducing and oxidizing activities, depending on the environment. Higher concentrations of vitamin C induce apoptotic cell death in various tumor cell lines including oral squamous cell carcinoma and salivary gland tumor cell lines, possibly via its pro-oxidant action. On the other hand, at lower concentrations, ascorbic acid displays an antioxidant property, preventing spontaneous, stress or anti-tumor agent-induced apoptosis. Intravenous administration of a Vitamin C derivative (Sodium 5,6-benzylidene-L-ascorbate), induces degeneration of human inoperable tumors and rat hepatocellular carcinoma in vivo, induces apoptotic or non-apoptotic cell death, depending on the types of target cells. On the other hand, elevation of intracellular concentration of ascorbic acid makes the cells resistant to the oxidative stress-induced apoptosis (Kang, J. H., Y. M. Shi, et al. (2000). "Effects of ascorbic acid and DL-alpha-tocopherol on human hepatoma cell proliferation and redifferentiation." *Acta Pharmacol Sin* 21(4): 348-52; Kang, J. H., Y. M. Shi, et al. (1999). "Effects of ascorbic acid on human hepatoma cell proliferation and redifferentiation." *Zhongguo Yao Li Xue Bao* 20(11): 1019-24).

Kang et al. showed that ascorbic acid can inhibit human hepatoma cell proliferation, induce redifferentiation, and reverse its malignant phenotype (Kang et al. 2000). They found cellular growth was inhibited by approximately 60% as compared to controls. The AFP level in these cells decreased from 302 to 90 (Kang et al. 1999; Kang et al. (2000)). Others have also found that ascorbic acid when used in combination with vitamin K, aloe vera, sodium selenite, or vitamin D has synergistic effects on hepatoma cells proliferation, re-differentiation, and reversal of malignant phenotype in vitro (Shamaan, Kadir et al. (1998); Wu and Chung (1998); Kang et al. (1999); Zhang, Y., P. Talalay, et al. (1992). "A major inducer of anticarcinogenic protective enzymes from broccoli: isolation and elucidation of structure." *Proc Natl Acad Sci USA* 89(6): 2399-403).

Example 5

The synergistic antioxidant activity of the composition may lower total body oxidative stress levels. Oxidative stress results in either decrease natural cell antioxidant capacity or an increased amount of reactive oxygen species (ROS) in organisms (Chu et al. (2002). "Antioxidant and Antiproliferative activities of Common Vegetables." *J. Agric. Food Chem.* 50: 6910-6916). This leads to increased DNA damage and mutations that could lead to development and/or expansion of cancer cells. The unique combination of ingredients in the composition may significantly lower ROS enough to prevent further cancer development. The antioxidant activity may also help increase natural DNA repair systems and increase normal liver regenerative activities.

Example 6

The composition causes significant decrease in the tumor marker AFP. AFP have been implicated in playing a role in keep the tumor cells hidden from the body's natural defense system. The composition may be "unmasking" the tumor cells by decreasing the AFP level and therefore allowing the body's natural immune system to recognize the tumor cells as not being normal and proceeding to kill those cells. Therefore the mechanism here would be to block or adversely effect AFP and enhance immune response against tumor cells.

These examples indicate that some of the active ingredients of said composition may either interfere or reverse the genetic alteration that is responsible for malignant transformation and continued uncontrolled growth for the cancer. It also appears that the composition may be able to induce rapid regeneration of normal liver cells. Tumor cell death and active liver regeneration are likely the result of the unique combination of active ingredients. In addition, the composition's nutritional support supplies the body's organs and potentially stimulates the immune system.

Although research has been performed with respect to some of the individual active ingredients of the invention, the composition has shown dramatic and unexpected clinical results not seen in previous studies. These results are likely due to the unique combination of active ingredients of the invention that likely have a synergistic effect and are able to confer clinical and therapeutic benefits to the patient. This unique combination provides excellent anti-cancer result with no ill side-effects. Furthermore, unlike the majority of the previous studies, the results presented herein have been demonstrated in humans.

This is a novel approach to supportive care, treatment, management, and prevention of cancer and other diseases of the liver. No current standard of care, treatment or method of prevention use the unique combination of ingredients described herein.

The preferred embodiments described herein are intended to illustrate the principles of the invention, but not to limit its scope. Other embodiments and variations to the preferred embodiments will be apparent to those skilled in the art and may be made without departing from the spirit and scope of the invention as defined in the fore-mentioned claims.

Although the instant disclosure sufficiently describes the invention, the numerous publications and patents cited herein may be of assistance in understanding the background of the invention and the state of the art. Accordingly, all of the publications and patents cited herein are hereby incorporated by reference into the present disclosure as if set forth in full herein.

We claim:

1. A composition comprising
between about 20 to about 26% *Brassica oleracea;*
between about 30 to about 36% *Daucus carota;*
between about 22 to about 28% *Apium* L.;
between about 0.1 to about 1.5% *Petroselinum crispum;*
between about 9 to about 15% *Spinacia oleracea* L;
between about 6 to about 12% *Beta vulgaris;*
between about 0.1 to about 1.5% aloe vera; and
between about 0.1 to 1.5% honey.

2. A dietary supplement comprising an effective amount of a claim 1.

3. The composition of claim 1, wherein the form of the composition is selected from the group consisting of an orally administered form, and an injectable form.

4. The composition of claim 3, wherein the composition is in the orally administered form and the orally administrable form is selected from a group consisting of a juice, a tablet, a powder, a suspension, an emulsion, a capsule, a granule, a troche, a pill, a liquid, a spirit, a syrup, and a limonade.

5. The composition of claim 3, wherein the composition is in the injectable form and the injectable form is selected from the group consisting of a liquid, a suspension, and a solution.

6. A pharmaceutical composition comprising a pharmaceutically effective amount of the composition of claim 1.

7. The pharmaceutical composition of claim 6, wherein the form of the composition is selected from a group consisting of an orally administered form and an injectable form.

8. The pharmaceutical composition of claim 7, wherein the composition is in the orally administered form and the orally administrable form is selected from a group consisting of a juice, a tablet, a powder, a suspension, an emulsion, a capsule, a granule, a troche, a pill, a liquid, a spirit, a syrup, and a limonade.

9. The pharmaceutical composition of claim 7, wherein the composition is in the injectable form and the injectable form is selected from the group consisting of a liquid, a suspension, and a solution.

10. The composition of claim 1, wherein the composition is administered as a dietary supplement.

11. The pharmaceutical composition of claim 6 comprising, a pharmaceutically acceptable carrier.

12. A composition mixture comprising
a *Brassica oleracea* component, said *Brassica oleracea* component comprises about 1031.48 mg potassium;
a *Apium graveolens* component, said *Apium graveolens* component comprises about 979.8 mg potassium;
a *Spinacia oleracea* component, said *Spinacia oleracea* component comprises about 885.1 mg potassium;
a *Daucus carota* component, said *Daucus carota* component comprises about 1043 mg potassium;
a *Beta vulgaris* component, said *Beta vulgaris* component comprises about 347.06 mg potassium;
a *Petroselinum crispum* component, said *Petroselinum crispum* component comprises about 89.46 mg potassium; and
a honey component, said honey component comprises about 11 mg potassium.

13. A composition mixture comprising
a *Brassica oleracea* component, said *Brassica oleracea* component comprises about 144.6 mg calcium;
a *Apium graveolens* component, said *Apium graveolens* component comprises about 136.3 mg calcium;
a *Spinacia oleracea* component, said *Spinacia oleracea* component comprises about 159.0 mg calcium;
a *Daucus carota* component, said *Daucus carota* component comprises about 119.2 mg calcium;
a *Beta vulgaris* component, said *Beta vulgaris* component comprises about 18.76 mg calcium;
a *Petroselinum crispum* component, said *Petroselinum crispum* component comprises about 21.3 mg calcium; and
a honey component, said honey component comprises about 1 mg calcium.

* * * * *